(12) United States Patent
Launer

(10) Patent No.: US 9,044,608 B2
(45) Date of Patent: Jun. 2, 2015

(54) SYSTEMS AND METHODS FOR FACILITATING ELECTRO-ACOUSTIC STIMULATION USING AN OFF-THE-EAR SOUND PROCESSOR MODULE

(75) Inventor: Stefan Launer, Zurich (CH)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/130,908

(22) PCT Filed: Jul. 8, 2011

(86) PCT No.: PCT/IB2011/053055
§ 371 (c)(1),
(2), (4) Date: Jan. 3, 2014

(87) PCT Pub. No.: WO2013/008057
PCT Pub. Date: Jan. 17, 2013

(65) Prior Publication Data
US 2014/0163628 A1   Jun. 12, 2014

(51) Int. Cl.
*A61N 1/36* (2006.01)
*H04R 25/04* (2006.01)
*A61N 1/372* (2006.01)
*H04R 25/00* (2006.01)

(52) U.S. Cl.
CPC ............ *A61N 1/36032* (2013.01); *H04R 25/04* (2013.01); *H04R 2430/03* (2013.01); *A61N 1/37252* (2013.01); *H04R 25/00* (2013.01)

(58) Field of Classification Search
CPC ............ A61N 1/36032; A61N 1/0541; A61H 39/002; A61H 2205/027
USPC ..................... 607/55–56, 136–137
See application file for complete search history.

(56) References Cited

U.S. PATENT DOCUMENTS

2005/0244026 A1\* 11/2005 Nielsen et al. ................. 381/380
2006/0287690 A1   12/2006 Bouchataoui et al.
2007/0106344 A1\* 5/2007 Darley et al. .................... 607/55

FOREIGN PATENT DOCUMENTS

DE   202008016880   3/2009

OTHER PUBLICATIONS

International Search Report and Written Opinion received in International Application No. PCT/IB11/053055 dated Mar. 16, 2012.
"Types of Cochlear Implants", *Alexander Graham Bell Association for the Deaf and Hard of Hearing*, http://nc.agbell.org/page.aspx?pid=728, as accessed Mar. 9, 2012.

\* cited by examiner

*Primary Examiner* — Paula J Stice
(74) *Attorney, Agent, or Firm* — ALG Intellectual Property, LLC

(57) ABSTRACT

An exemplary electro-acoustic stimulation ("EAS") system (100) includes 1) an off-the-ear sound processor module (102), 2) a headpiece module (104) communicatively coupled directly to the off-the-ear sound processor module (102) and configured to be affixed to a head of a patient, the headpiece module (104) comprising a housing with communication circuitry disposed therein that is configured to facilitate communication by the off-the-ear sound processor module (102) with a cochlear implant (106) implanted within the patient, and 3) a loudspeaker (110) communicatively coupled directly to the headpiece module (104). The off-the-ear sound processor module (102) is configured to direct the cochlear implant (106) to apply electrical stimulation to the patient and direct the loudspeaker (110) to apply acoustic stimulation to the patient. Corresponding systems, devices, and methods are also disclosed.

20 Claims, 7 Drawing Sheets

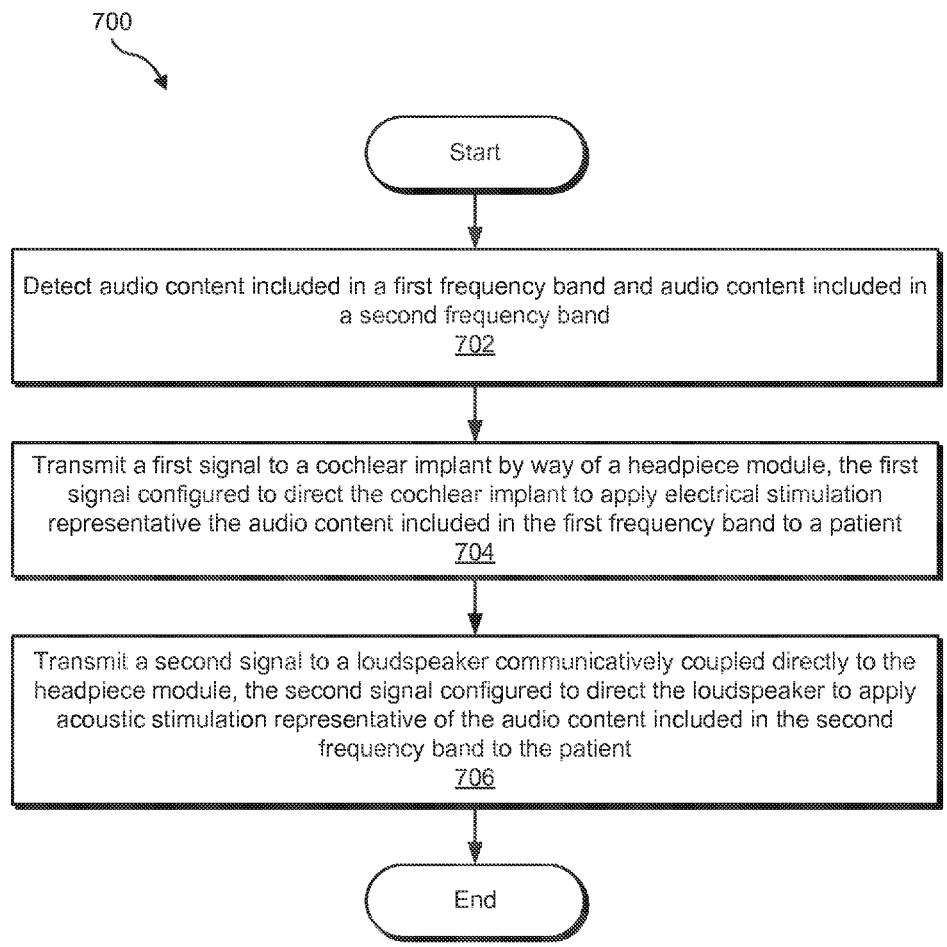

SYSTEMS AND METHODS FOR FACILITATING ELECTRO-ACOUSTIC STIMULATION USING AN OFF-THE-EAR SOUND PROCESSOR MODULE

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the cochlea are impeded. These sound pathways may be impeded, for example, by damage to the ossicular chain, excessive sew men, or a malformed Typanic Membrane. Mild conductive hearing losses can be treated with hearing aids, while stronger losses may require a middle ear surgery or a Bone Anchored Hearing Aid ("BAHA").

Sensorineural hearing loss, on the other hand, is primarily caused by the absence or destruction of the outer and/or inner hair cells on the basilar membrane. There are rare cases in which sensorineural hearing loss is caused by a malfunction of the vestibulacochlear nerve or even the central processing system. To overcome sensorineural hearing loss, numerous cochlear implant systems—or cochlear prostheses—have been developed. Cochlear implant systems bypass the major part of the ear by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function. Cochlear implants are typically capable of providing high-frequency information up to 8 kHz.

There is a certain group of people that has some degree of residual hearing in the low frequencies (e.g., below 1 kHz) and a severe hearing loss in the high frequencies (e.g., above 1 kHz). These people cannot benefit from traditional amplification because of the severity of the hearing loss in the high frequencies. Nor are they classic cochlear implant candidates, because of their mostly intact low frequency residual hearing.

For this group of people, various electro-acoustic stimulation ("EAS") systems have been developed that provide such patients with the ability to perceive both low and high frequencies. Electra-acoustic stimulation refers to the use of a hearing aid and a cochlear implant together in the same ear. The hearing aid acoustically amplifies the low frequencies while the cochlear implant electrically stimulates the high frequencies. The auditory nerve combines the acoustic and electric stimuli to one auditory signal. Results of various studies have shown a highly synergistic effect between hearing aid and cochlear implant technology, particularly evident in speech understanding, pitch discrimination, and music appreciation.

However, traditional electro-acoustic stimulation systems require the use of a sound processor worn on or behind the ear of a patient. Such sound processors are often large, bulky, and aesthetically unpleasing. Moreover, they are difficult or impossible to use with pediatric patients (e.g., small children or infants). Hence, in many cases, it would be desirable to use an off-the-ear sound processor (e.g., a body-worn sound processor) when providing EAS functionality to a patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 7 illustrates an exemplary method of facilitating electro-acoustic stimulation using an off-the-ear sound processor module according to principles described herein.

SUMMARY

Figure 1:
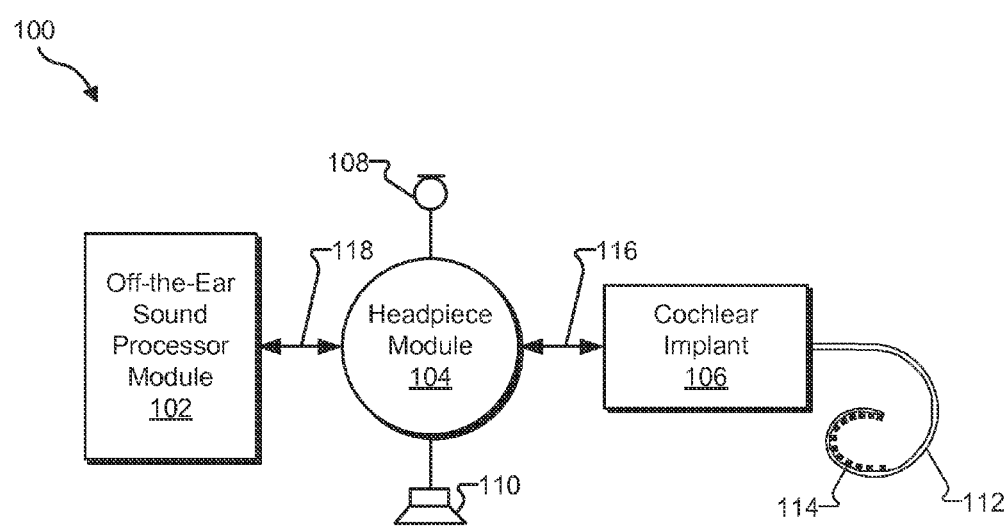
FIG. 1 illustrates an exemplary electro-acoustic stimulation ("EAS") system according to principles described herein.

An exemplary electro-acoustic stimulation ("EAS") system includes 1) an off-the-ear sound processor module, 2) a headpiece module communicatively coupled directly to the off-the-ear sound processor module and configured to be affixed to a head of a patient, the headpiece module comprising a housing with communication circuitry disposed therein that is configured to facilitate communication by the off-the-ear sound processor module with a cochlear implant implanted within the patient, and 3) a loudspeaker communicatively coupled directly to the headpiece module. The off-the-ear sound processor module is configured to direct the cochlear implant to apply electrical stimulation to the patient and direct the loudspeaker to apply acoustic stimulation to the patient.

An exemplary device includes 1) a detection facility configured to detect audio content included in a first frequency band and audio content included in a second frequency band, 2) an electrical stimulation management facility communicatively coupled to the detection facility and configured to direct, by way of a headpiece module communicatively coupled to the device, a cochlear implant to apply electrical stimulation representative the audio content included in the first frequency band to a patient, and 3) an acoustic stimulation management facility communicatively coupled to the detection facility and configured to direct, by way of the headpiece module, a loudspeaker communicatively coupled directly to the headpiece module to apply acoustic stimulation representative of the audio content included in the second frequency band to the patient.

An exemplary method includes an off-the-ear sound processor module 1) detecting audio content included in a first frequency band and audio content included in a second frequency band, 2) transmitting a first signal to a cochlear implant by way of a headpiece module communicatively coupled directly to the off-the-ear sound processor module, the first signal configured to direct the cochlear implant to apply electrical stimulation representative the audio content included in the first frequency band to a patient, and 3) transmitting a second signal to a loudspeaker communicatively coupled directly to the headpiece module, the second signal configured to direct the loudspeaker to apply acoustic stimulation representative of the audio content included in the second frequency band to the patient.

DETAILED DESCRIPTION

Systems and methods for facilitating electro-acoustic stimulation using an off-the-ear sound processor module are described herein. As will be described below, an exemplary electro-acoustic stimulation ("EAS") system may include 1) an off-the-ear sound processor module, 2) a headpiece module communicatively coupled directly to the off-the-ear sound processor module and comprising a housing with communication circuitry disposed therein that is configured to facilitate communication by the off-the-ear sound processor module with a cochlear implant implanted within a patient, and 3) a loudspeaker communicatively coupled directly to the headpiece module. In this configuration, the off-the-ear sound processor module may direct the cochlear implant to apply electrical stimulation (e.g., electrical stimulation representative of audio content included in a relatively high frequency band) to the patient and direct the loudspeaker to apply acoustic stimulation (e.g., acoustic stimulation representative of audio content included in a relatively low frequency band) to the patient.

Numerous advantages may be associated with the systems and methods described herein. For example, the systems and methods described herein may facilitate electro-acoustic stimulation of a patient using an off-the-ear sound processor module, which may be capable of increased signal processing capabilities compared to a traditional behind-the-ear ("BTE") sound processing unit. Moreover, the systems and methods described herein may provide a more aesthetically pleasing experience for EAS patients, enable pediatric patients to enjoy the benefits provided by EAS systems heretofore not available to them, and provide additional benefits that will become apparent herein.

FIG. 1 illustrates an exemplary EAS system 100. EAS system 100 may include an off-the-ear sound processor module 102 (or simply "sound processor module 102"), a headpiece module 104, a cochlear implant 106, a microphone 108, a loudspeaker 110, and a lead 112 having a plurality of electrodes 114 disposed thereon. Sound processor module 102, headpiece module 104, and cochlear implant 106 may each include or be implemented by any combination of hardware, software, and/or firmware as may serve a particular implementation. For example, sound processor module 102 may include or be implemented by a computing device or processor configured to perform one or more of the functions described herein. Each of the components shown in FIG. 1 will now be described in more detail.

Sound processor module 102 (also referred to as an EAS device) is configured to be worn off the ear of a patient. In other words, sound processor module 102 may be worn or carried by a patient at any location other than behind or on the ear. For example, sound processor module 102 may be secured to a piece of clothing worn by the patient, carried in a pocket or pouch, and/or otherwise carried by the patient. Because sound processor module 102 is not worn behind or on the ear, sound processor module 102 may be relatively larger than typical behind-the-ear sound processors and may therefore include additional or enhanced features compared to such typical behind-the-ear sound processors. Various components and features of sound processor module 102 will now be described.

Figure 2:
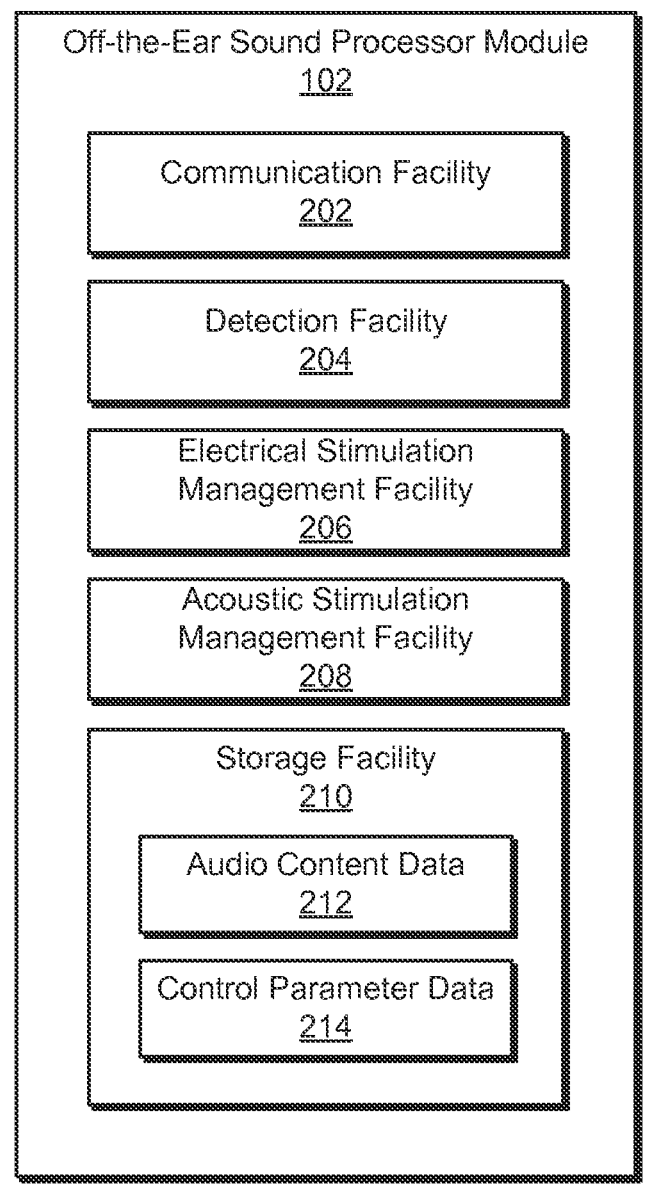
FIG. 2 illustrates exemplary components of sound processor module according to principles described herein.

FIG. 2 illustrates exemplary components of sound processor module 102. As shown in FIG. 2, sound processor module 102 may include a communication facility 202, a detection facility 204, an electrical stimulation management facility 206, an acoustic stimulation management facility 208, and a storage facility 210, which may be in communication with one another using any suitable communication technologies. Each of these facilities may include any combination of hardware, software, and/or firmware as may serve a particular implementation. For example, one or more of facilities may include at least one computing device or processor configured to perform one or more of the functions described herein. Facilities 202-210 will now be described in more detail.

Communication facility 202 may be configured to facilitate communication between sound processor module 102 and cochlear implant 106. For example, communication facility 202 may include transceiver components configured to wirelessly transmit data (e.g., control parameters and/or power signals) to cochlear implant 106 and/or wirelessly receive data from cochlear implant 106 by way of communication circuitry disposed within headpiece module 104.

Detection facility 204 may be configured to detect audio content presented to a patient (e.g., one or more audio signals received by microphone 108) and one or more attributes associated with the audio content. For example, detection facility 204 may determine whether the detected audio content is included in a "high" frequency band (e.g., a frequency band substantially equal to 1 kHz-8 kHz) or in a "low" frequency band (e.g., a frequency band substantially equal to 100 Hz-1 kHz). It will be recognized that the particular frequencies associated with the high and low frequency bands may vary as may serve a particular implementation.

Electrical stimulation management facility 206 may be configured to perform one or more electrical stimulation management operations. For example, electrical stimulation management facility 206 may be configured to direct, by way of a headpiece module 104, cochlear implant 106 to apply electrical stimulation representative audio content included in the high frequency band to a patient. The directing may be performed in any suitable manner. For example, electrical stimulation management facility 206 may direct cochlear implant 106 to apply the electrical stimulation by transmitting one or more signals to cochlear implant 106 by way of headpiece module 104.

Acoustic stimulation management facility 208 may be configured to perform one or more acoustic stimulation management operations. For example, acoustic stimulation management facility 208 may be configured to direct, by way of a headpiece module 104, loudspeaker 110 to apply acoustic stimulation representative audio content included in the low frequency band to the patient. The directing may be performed in any suitable manner. For example, acoustic stimulation management facility 208 may direct loudspeaker 110 to apply the acoustic stimulation by transmitting one or more signals to loudspeaker 110 by way of headpiece module 104.

Storage facility 210 may be configured to maintain audio content data 212 representative of or otherwise associated with audio content detected by detection facility 204 and control parameter data 214 representative of one or more control parameters that may be transmitted to cochlear implant 106. Storage facility 210 may be configured to maintain additional or alternative data as may serve a particular implementation.

Returning to FIG. 1, headpiece module 104 may be configured to be affixed to a patient's head and positioned such that communication circuitry (e.g., a coil) housed within headpiece module 104 is communicatively coupled to corresponding communication circuitry (e.g., a coil) included within cochlear implant 106. In this manner, headpiece module 104 may be communicatively coupled to cochlear implant 106 in a wireless manner, as illustrated by communication link 116.

Headpiece module 104 may also be communicatively coupled directly to sound processor module 102, as illustrated by communication link 118. Communication link 118 may be wired (e.g., implemented by one or more wires, cables, etc.) or wireless as may serve a particular implementation.

Communication links 116 and 118 may facilitate communication between sound processor module 102 and cochlear implant 106. For example, sound processor module 102 may direct cochlear implant 106 to apply electrical stimulation representative of audio content by routing one or more signals to cochlear implant 106 by way of communication link 118, headpiece module 104, and then communication link 116.

Headpiece module 104 may also be communicatively coupled to microphone 108 and loudspeaker 110. Microphone 108 may be configured to receive (e.g., detect) one or more audio signals presented to a patient for processing by sound processor module 102. To this end, microphone 108 may be communicatively coupled to sound processor module 102 by communication channel 118 and/or in any other manner as may serve a particular implementation. In some examples, as will be illustrated in more detail below, microphone 108 may be at least partially disposed within the housing of headpiece module 104. In some alternative embodiments, microphone 108 may be positioned near or within the ear canal or coupled directly to sound processor module 102.

Loudspeaker 110 (also referred to as a receiver) may be communicatively coupled directly to headpiece module 104 and configured to apply acoustic stimulation to a patient. For example, loudspeaker 110 may present an amplified version of audio content included in a low frequency band to the patient.

Loudspeaker 110 may be communicatively coupled directly to headpiece module 104 in any suitable manner. For example, as will be illustrated in more detail below, loudspeaker 110 may be at least partially disposed within the housing of headpiece module 104. Alternatively, loudspeaker 110 may be at least partially integrated into an earmold configured to be located within the outer ear of the patient and communicatively coupled directly to headpiece module 104 with one or more wires.

Cochlear implant 106, lead 112, and electrodes 114 may be partially or fully implanted within a patient and configured to apply electrical stimulation to one or more stimulation sites associated with an auditory pathway (e.g., the auditory nerve) of the patient. Cochlear implant 106 may include any type of implantable stimulator that may be used in association with the systems and methods described herein.

Figure 3:
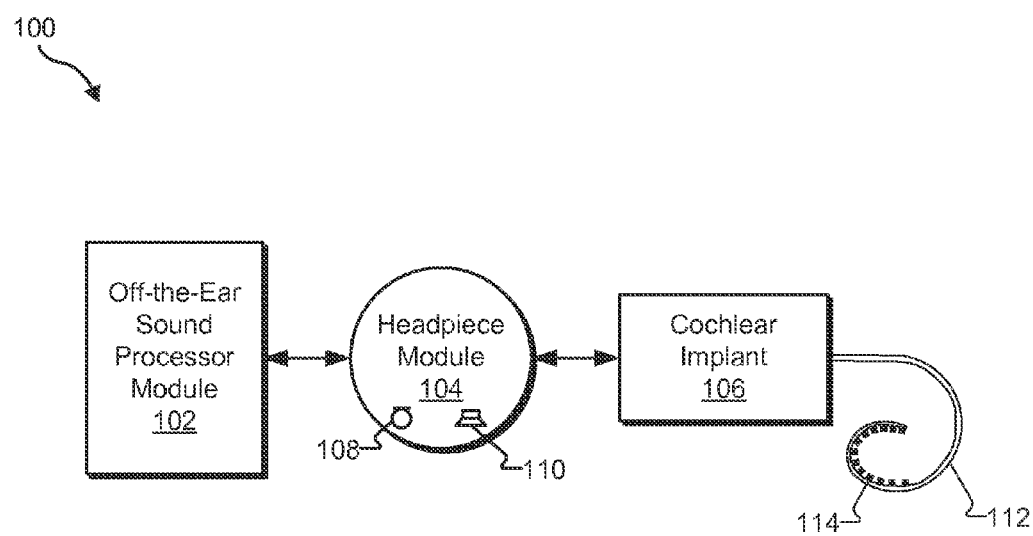
FIG. 3 illustrates an exemplary configuration of the EAS system of FIG. 1 according to principles described herein.

FIG. 3 illustrates an exemplary configuration of EAS system 100 wherein microphone 108 and loudspeaker 110 are both at least partially disposed with a housing of headpiece module 104. In this configuration, acoustic stimulation generated by loudspeaker 110 may be routed to the ear canal of a patient with an acoustic tube.

Figure 4:
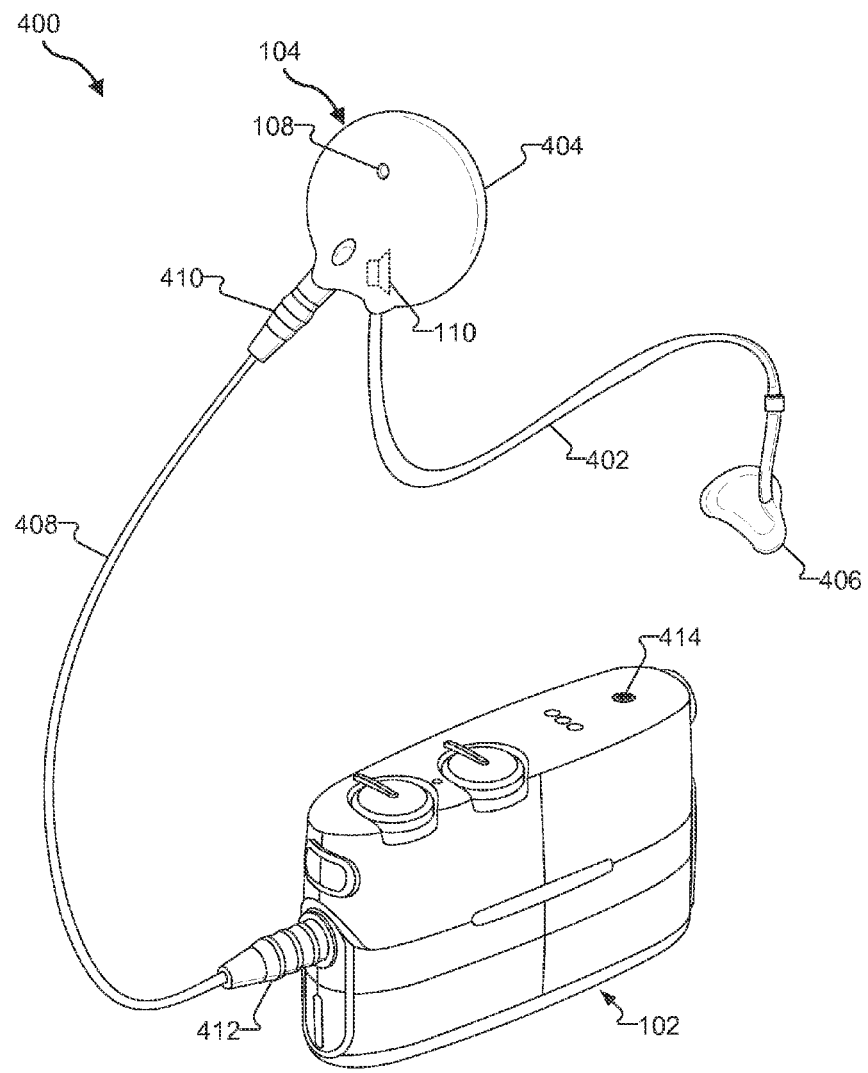
FIG. 4 shows an exemplary implementation of the system of FIG. 1 wherein an acoustic tube is configured to route acoustic stimulation generated by a loudspeaker to an ear canal of a patient according to principles described herein.

To illustrate, FIG. 4 shows an exemplary implementation 400 of system 100 wherein an acoustic tube 402 is configured to route acoustic stimulation generated by loudspeaker 110 to an ear canal of a patient. As illustrated by the dashed lines, loudspeaker 110 may be entirely disposed within a housing 404 of headpiece module 104.

Acoustic tube 402 may be connected at a proximal end to loudspeaker 110 and at a distal end to an earmold 406 configured to be located within the outer ear of the patient. In this manner, acoustic tube 402 may route sound (i.e., acoustic stimulation) generated by loudspeaker 110 to the ear canal of the patient.

Earmold 406 may include any type of earmold that may be at least partially disposed within the outer ear of the patient. For example, earmold 406 may include an open dome configured to allow the ear to remain partially open (e.g., an open dome tip made from a soft silicone material and configured to resemble a tulip or flower bud), a closed dome configured to entirely close off the ear canal, a foam dome, and/or any other type of dome as may serve a particular implementation.

Acoustic tube 402 may be made out of any suitable material configured to facilitate the transmission of sound. In some examples, acoustic tube 402 may be selective removed or otherwise bypassed, For example, acoustic tube 402 may be removed or otherwise bypassed if the patient desires to utilize EAS system 100 without the use of earmold 406.

FIG. 4 also shows that headpiece module 104 may be removably coupled to sound processor module 102. For example, as shown in FIG. 4, headpiece module 104 may be coupled to sound processor module 102 by way of cable 408, To this end, headpiece module 104 and sound processor module 102 may each include a connector port (not shown) configured to connect to corresponding connectors 410 and 412 of cable 408. When a user desires to disconnect headpiece module 104 from sound processor module 102, he or she may remove connector 412 of cable 408 from the connector port of sound processor module 102 and/or connector 410 of cable 408 from the connector port of headpiece module 104.

As shown in FIG. 4, microphone 108 may be integrated into a surface of housing 404. Audio content detected by microphone 108 may be routed to sound processer module 102 by way of cable 408 and/or in any other manner. In some embodiments, sound processor module 102 may additionally or alternatively include an auxiliary audio input port 414 configured to receive auxiliary audio content (e.g., from an auxiliary audio input device such as an MP3 player, an FM transmitter, and/or any other device configured to provide audio input that may be processed by sound processor module 102). Electrical and/or acoustic stimulation representative of the auxiliary audio content may be applied to the patient as described herein.

Figure 5:
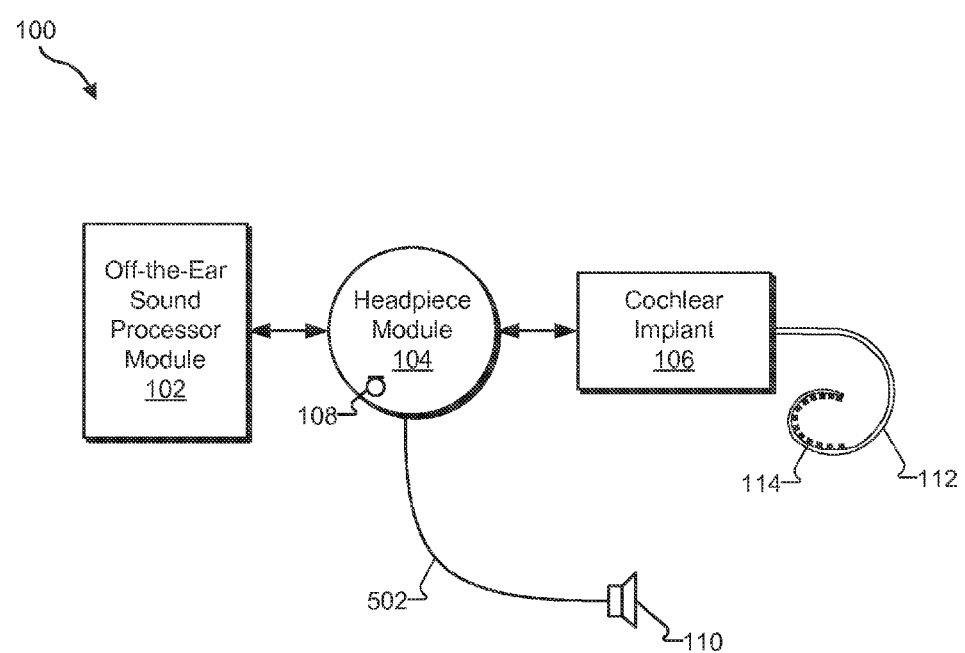
FIG. 5 illustrates another exemplary configuration of the EAS system of FIG. 1 according to principles described herein.

FIG. 5 illustrates another exemplary configuration of EAS system 100 wherein loudspeaker 110 is configured to be located external to headpiece module 104. As shown, loudspeaker 110 may be communicatively coupled directly to headpiece module 104 (e.g., to circuitry included within the housing of headpiece module 104) with one or more wires (e.g., wire 502).

Figure 6:
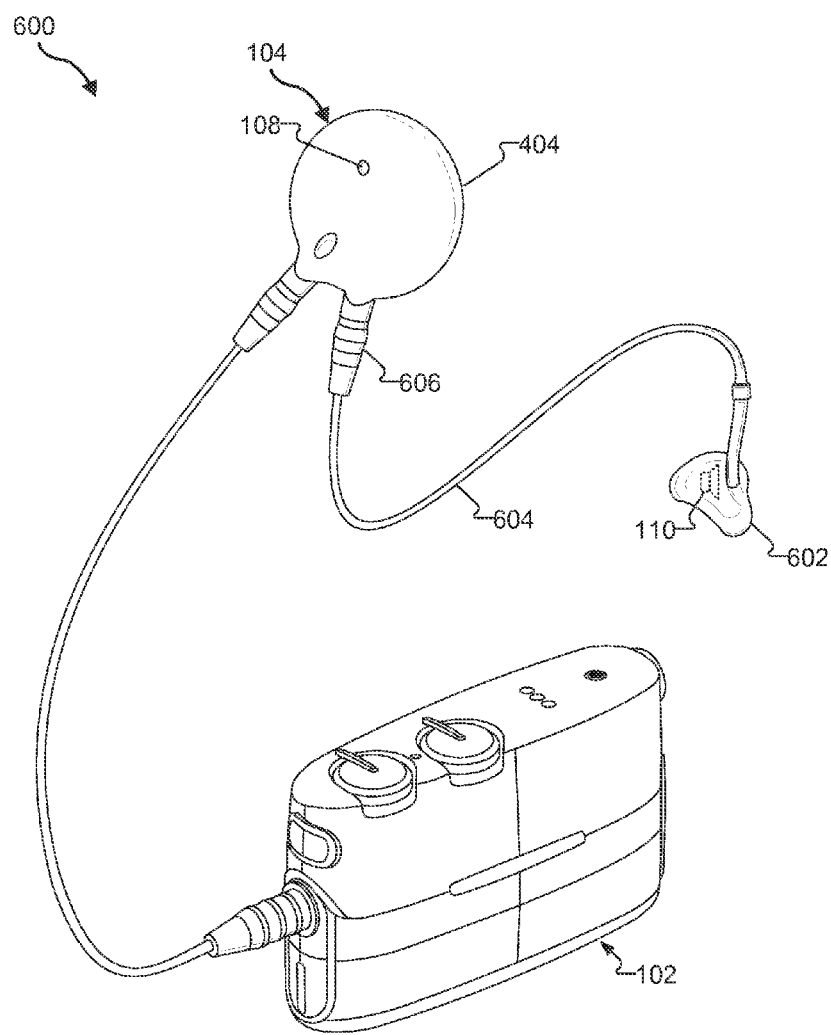
FIG. 6 shows an exemplary implementation of the system of FIG. 1 wherein a loudspeaker is at least partially integrated into an earmold configured to be located within the outer ear of the patient according to principles described herein.

To illustrate, FIG. 6 shows an exemplary implementation 600 of system 100 wherein loudspeaker 110 is at least partially integrated into an earmold 602 configured to be located within the outer ear of the patient. Loudspeaker 110 is represented by dashed lines in FIG. 6 to illustrate that it has been integrated into earmold 602. A cable 604 comprising one or more wires (not shown) may be configured to communicatively removably couple loudspeaker 110 to headpiece module 104. To this end, headpiece module 104 may include a connector port (not shown) configured to connect to a corresponding connector 606 of cable 604. Implementation 600 may be beneficial when it is desired for loudspeaker 110 to be located within the ear.

FIG. 7 illustrates an exemplary method 700 of facilitating electro-acoustic stimulation using an off-the-ear sound processor module. While FIG. 7 illustrates exemplary steps according to one embodiment, other embodiments may omit, add to, reorder, and/or modify any of the steps shown in FIG.

7. One or more of the steps shown in FIG. 7 may be performed by any component or combination of components of sound processor module 104.

In step 702, the off-the-ear sound processor module communicatively coupled directly to a headpiece module detects audio content included in a first frequency band and audio content included in a second frequency band. Step 702 may be performed in any of the ways described herein.

In step 704, the off-the-ear sound processor module transmits a first signal to a cochlear implant by way of a headpiece module. The first signal is configured to direct the cochlear implant to apply electrical stimulation representative the audio content included in the first frequency band to a patient. Step 704 may be performed in any of the ways described herein.

In step 706, the off-the-ear sound processor module transmits a second signal to a loudspeaker communicatively coupled directly to the headpiece module. The second signal is configured to direct the loudspeaker to apply acoustic stimulation representative of the audio content included in the second frequency band to the patient. Step 706 may be performed in any of the ways described herein.

It will be recognized that the systems and methods described herein may be applied to a bilateral EAS system configuration electrical and acoustic stimulation may be applied to both ears of the patient. For example, sound processor module 102 may be directly coupled to a first headpiece associated with the right ear of the patient and to a second headpiece associated with the left ear of the patient. Each headpiece may be wirelessly connected to a distinct cochlear implant configured to provide electrical stimulation to its associated ear and directly connected to a distinct loudspeaker configured to provide acoustic stimulation to its associated ear.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An electro-acoustic stimulation ("EAS") system comprising:
   an off-the-ear sound processor module;
   a headpiece module communicatively coupled directly to the off-the-ear sound processor module and configured to be affixed to a head of a patient, the headpiece module comprising a housing with communication circuitry disposed therein that is configured to facilitate communication by the off-the-ear sound processor module with a cochlear implant implanted within the patient; and
   a loudspeaker communicatively and physically coupled directly to the headpiece module;
   wherein the off-the-ear sound processor module is configured to direct the cochlear implant to apply electrical stimulation to the patient and direct the loudspeaker to apply acoustic stimulation to the patient.

2. The EAS system of claim 1, wherein the loudspeaker is at least partially disposed within the housing of the headpiece module.

3. The EAS system of claim 2, further comprising an acoustic tube coupled to the loudspeaker and to an earmold configured to be located within the outer ear of the patient, the acoustic tube configured to route the acoustic stimulation to the patient.

4. The EAS system of claim 1, wherein the loudspeaker is configured to be:
   at least partially integrated into an earmold configured to be located within the outer ear of the patient; and
   communicatively coupled directly to the headpiece module with one or more wires.

5. The EAS system of claim 4, wherein the one or more wires are disposed within a cable, and wherein the headpiece module comprises a port configured to receive the cable.

6. The EAS system of claim 1, wherein:
   the headpiece module further comprises a microphone at least partially disposed within the housing, the microphone configured to detect audio content presented to the patient; and
   the electrical stimulation and the acoustic stimulation are each representative of a portion of the audio content.

7. The EAS system of claim 1, wherein the off-the-ear sound processor module comprises an auxiliary audio input port configured to receive auxiliary audio content, and wherein the electrical stimulation and the acoustic stimulation are each representative of a portion of the auxiliary audio content.

8. The EAS system of claim 1, wherein the off-the-ear sound processor module is configured to direct the cochlear implant to apply electrical stimulation to the patient by transmitting one or more signals to the cochlear implant by way of the headpiece module.

9. The EAS system of claim 1, wherein the off-the-ear sound processor module is configured to direct the loudspeaker to apply acoustic stimulation to the patient by transmitting one or more signals to the loudspeaker by way of the headpiece module.

10. The EAS system of claim 1, wherein the electrical stimulation is representative of audio content included in a first frequency band and the acoustic stimulation is representative of audio content included in a second frequency band.

11. The EAS system of claim 10, wherein the first frequency band is higher than the second frequency band.

12. A device comprising:
   a detection facility configured to detect audio content included in a first frequency band and audio content included in a second frequency band;
   an electrical stimulation management facility communicatively coupled to the detection facility and configured to direct, by way of a headpiece module communicatively coupled to the device, a cochlear implant to apply electrical stimulation representative the audio content included in the first frequency band to a patient; and
   an acoustic stimulation management facility communicatively coupled to the detection facility and configured to direct, by way of the headpiece module, a loudspeaker communicatively and physically coupled directly to the headpiece module to apply acoustic stimulation representative of the audio content included in the second frequency band to the patient.

13. The device of claim 12, wherein the device is communicatively coupled directly to the headpiece module.

14. The device of claim 12, wherein:
   the device is configured to be worn by the patient off the ear; and
   the headpiece module is configured to be affixed to a head of the patient.

15. The device of claim 12, wherein the first frequency band is higher than the second frequency band.

16. The device of claim 12, wherein the audio content comprises auxiliary audio content provided by an auxiliary audio input device.

17. A method comprising:
- detecting, by an off-the-ear sound processor module communicatively coupled directly to a headpiece module, audio content included in a first frequency band and audio content included in a second frequency band;
- transmitting, by the off-the-ear sound processor module, a first signal to a cochlear implant by way of the headpiece module, the first signal configured to direct the cochlear implant to apply electrical stimulation representative the audio content included in the first frequency band to a patient; and
- transmitting, by the off-the-ear sound processor module, a second signal to a loudspeaker communicatively and physically coupled directly to the headpiece module, the second signal configured to direct the loudspeaker to apply acoustic stimulation representative of the audio content included in the second frequency band to the patient.

18. The method of claim 17, wherein:
- the off-the-ear sound processor module is configured to be worn by the patient off the ear; and
- the headpiece module is configured to be affixed to a head of the patient.

19. The method of claim 17, wherein the first frequency band is higher than the second frequency band.

20. The method of claim 17, wherein the audio content comprises auxiliary audio content provided by an auxiliary audio input device.

\* \* \* \* \*